(12) United States Patent
Sun

(10) Patent No.: US 7,829,772 B2
(45) Date of Patent: Nov. 9, 2010

(54) FLUORESCENT CARBON NANOPARTICLES

(75) Inventor: Ya-Ping Sun, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 283 days.

(21) Appl. No.: 11/814,410

(22) PCT Filed: Oct. 27, 2006

(86) PCT No.: PCT/US2006/042233

§ 371 (c)(1), (2), (4) Date: Jul. 20, 2007

(87) PCT Pub. No.: WO2007/050984

PCT Pub. Date: May 3, 2007

(65) Prior Publication Data

US 2008/0113448 A1 May 15, 2008

Related U.S. Application Data

(60) Provisional application No. 60/730,790, filed on Oct. 27, 2005.

(51) Int. Cl.
*G01N 33/543* (2006.01)
(52) U.S. Cl. ............. 977/773; 436/518; 436/523; 977/700; 977/702; 977/703; 977/704; 977/705
(58) Field of Classification Search .................. None
See application file for complete search history.

(56) References Cited

U.S. PATENT DOCUMENTS

| | | | |
|---|---|---|---|
| 5,429,824 A * | 7/1995 | June | 424/489 |
| 5,537,000 A | 7/1996 | Alivisatos et al. | |
| 5,547,748 A * | 8/1996 | Ruoff et al. | 428/323 |
| 5,861,349 A | 1/1999 | Vereschagin et al. | |
| 5,866,434 A | 2/1999 | Massey et al. | |
| 5,916,955 A | 6/1999 | Vereschagin et al. | |
| 5,922,537 A * | 7/1999 | Ewart et al. | 435/6 |
| 6,322,901 B1 | 11/2001 | Bawendi et al. | |
| 6,361,660 B1 | 3/2002 | Goldstein | |
| 6,468,808 B1 | 10/2002 | Nie et al. | |
| 6,495,258 B1 | 12/2002 | Chen et al. | |
| 6,593,137 B1 * | 7/2003 | Erlanger et al. | 435/345 |
| 6,608,716 B1 | 8/2003 | Armstrong et al. | |
| 6,649,138 B2 * | 11/2003 | Adams et al. | 423/403 |
| 6,710,366 B1 | 3/2004 | Lee et al. | |
| 6,794,265 B2 | 9/2004 | Lee et al. | |
| 6,821,337 B2 | 11/2004 | Bawendi et al. | |
| 6,846,565 B2 | 1/2005 | Korgel et al. | |
| 6,855,551 B2 | 2/2005 | Bawendi et al. | |
| 6,861,155 B2 | 3/2005 | Bawendi et al. | |
| 6,918,946 B2 | 7/2005 | Korgel et al. | |
| 7,004,310 B2 | 2/2006 | Axmann | |
| 7,005,229 B2 | 2/2006 | Nirmal et al. | |
| 7,005,669 B1 | 2/2006 | Lee | |
| 7,125,605 B2 | 10/2006 | Bawendi et al. | |
| 7,138,098 B2 | 11/2006 | Bawendi et al. | |
| 7,235,361 B2 | 6/2007 | Bawendi et al. | |
| 2003/0003300 A1 * | 1/2003 | Korgel et al. | 428/402 |
| 2003/0008414 A1 | 1/2003 | Nie et al. | |
| 2003/0042850 A1 | 3/2003 | Betram et al. | |
| 2003/0227116 A1 | 12/2003 | Halik et al. | |
| 2004/0091635 A1 | 5/2004 | Yaniv | |
| 2004/0229447 A1 | 11/2004 | Swihart et al. | |
| 2004/0252488 A1 | 12/2004 | Thurk | |
| 2005/0123974 A1 | 6/2005 | Gilmanshin et al. | |
| 2005/0191647 A1 | 9/2005 | Meyer-Almes | |
| 2005/0201963 A1 | 9/2005 | Dutta | |
| 2005/0250141 A1 | 11/2005 | Lambert et al. | |
| 2005/0267345 A1 | 12/2005 | Korgel et al. | |
| 2005/0287548 A1 | 12/2005 | Bao et al. | |
| 2006/0003465 A1 | 1/2006 | Zhukov et al. | |
| 2006/0078490 A1 | 4/2006 | Shih et al. | |
| 2006/0173362 A1 | 8/2006 | Toms et al. | |
| 2007/0082411 A1 | 4/2007 | Muys | |
| 2008/0113448 A1 | 5/2008 | Sun | |

FOREIGN PATENT DOCUMENTS

WO  WO 2009/009630  1/2009

OTHER PUBLICATIONS

Taylor et al. Synthesis and characterization of peptide-functionalized polymeric nanoparticles. Biomacromolecules (2004) 5:245-248.*

(Continued)

*Primary Examiner*—Unsu Jung
*Assistant Examiner*—Leon Y. Lum
(74) *Attorney, Agent, or Firm*—Dority & Manning, P.A.

(57) ABSTRACT

Disclosed are photoluminescent particles. The particles include a core nano-sized particle of carbon and a passivation agent bound to the surface of the nanoparticle. The passivation agent can be, for instance, a polymeric material. The passivation agent can also be derivatized for particular applications. For example, the photoluminescent carbon nanoparticles can be derivatized to recognize and bind to a target material, for instance a biologically active material, a pollutant, or a surface receptor on a tissue or cell surface, such as in a tagging or staining protocol.

41 Claims, 9 Drawing Sheets

OTHER PUBLICATIONS

Ma, et al., "Fluorescence spectra and quantum yields of [60] fullerene and [70] fullerene under different solvent conditions. A quantitative examination using a near-infrared-sensitive emission spectrometer", J. Chem. Soc., Perkin Trans., 2, pp. 2157-2162 (1996).

Riggs, et al., "Strong Luminescence of Solubilized Carbon Nanotubes", J. American Chem. Soc. 122, pp. 5879-5880, (2000).

Sun, et al., "Preparation and Characterization of Highly Water-Soluble Pendant Fullerene Polymers", Macromolecules, 32, pp. 8747-8752, (1999).

Sun, et al., "Preparation and Characterization of a Highly Water-Soluble Pendant Fullerene Polymer", Chem. Commun., pp. 2699-2700, (1996).

J.S. Biteen et al.—Controlled Passivation and Luminescence Blue Shifts of Isolated Silicon Nanocrystals—*Mat.Res. Soc. Symp. Proc.* vol. 770 2003.

I.N. Germanenko et al.—Effect of atomospheric oxidation on the electronic and photoluminescence properties of silicon nanocrystals—*Pure Appl. Chem.*, vol. 72, Nos. 1-2, pp. 245-255, 2000.

M.V. Wolkkin et al.—Abstract of Electronic States and Luminescence in Pourous Silicon Quantum Dots: The Role of Oxygen—Smithsonian?NASA ADS Physics Abstract Service—*The American Physical Socoiety* 10.1103/PhysRevLett.82.197 1999.

Holmes et al.—Highly Luminescent Silicon Nanocrystals with Discrete Optical Transitions—*J.Am. Chem. Soc. 2001*, 123, 3743-3748.

Y. Suda et al.—Preparation of carbon nanoparticles by plasma-assisted pulsed laser deposition method—size and binding energy dependence on ambient gas pressure and plasma condition—*Elsevier Thin Solid Fims 415* (2002) 15-20.

Z.F. Li et al.—Abstract—Water-Soluble Poly(acrylic acid) Grafted Luminescent Silicon Nanoparticles and Their Use as Fluorescent Biological Staining Labels—*Dept. of Chem. & Bio. Eng.,* St. Univers. of NY at Buffalo, 2004.

S. Louie—Quantum Confinement and Optical Gaps in Si Nanocrystals—*Phys.Rev.Let. 79*, 1997.

X. Li et al.—Process for Preparing Macroscopic Quantities of Brightly Photoluminescent Silicon Nanoparticles with Emission Spanning the Visible Spectrum—*Langmuir 2003*, 19, 8490-8496.

Fernando, et al., High Aqueous Solubility of Functionalized Single-Walled Carbon Nanotubes, *Longmuir*, 2004, 20 (11), pp. 4777-4778.

Huang, et al., "Solubilization of Single-Walled Carbon Nanotubes with Diamine-Terminated Oligomeric Poly(ethylene Glycol) in Different Functionalization Reaction", *Nano Letters*, 2003, 3(4), p. 565,568.

Larson et al., "Water-Soluble Quantum Dots for Multiphoton Fluorescence Imaging in Vivo", *Science*, vol. 300, pp. 1434-1436, (2003).

Grecco, et al., "Ensemble and Single Particle Photophysical Properties (Two-Photon Excitation, Anisotropy, FRET, Lifetime, Spectral Conversion) of Commercial Quantum Dots in Solution and in Live Cells", *Microscopy Research and Technique*, (2004) 65:169-179.

Padilha, et al., "Frequency Degenerate and Nondegenerate Two-Photon Absorption Spectra of Semiconductor Quantum Dots", *Physical Review*B, (2007), 75, 075325.

Clapp, et al., "Two-Photon Excitation of Quantum Dot Donors in Fluorescence Resonance Energy Transfer Applications" Conference on Bioanotechnology on Nov. 16, 2006, San Francisco.

Pu, et al., "The Empirical Correlation Between Size and Two-Photon Absorption Cross Section of CdSe and CdTe Quantum Dots", *Small*, (2006), vol. 2, No. 11, pp. 1308-1313.

Ma, et al., "Plasma synthesis of carbon magnetic nanoparticles and immobilization of doxorubicin for targeted drug delivery", *J. Biomater. Sci. Polymer Rdn.*, vol. 13, No. 8, pp. 1033-1049 (2004).

Schick, et al., "Unusual Luminescence of Hexapyrrolidine Derivatives of $C_{60}$ with $T_h$ and Novel $D_3$-Symmetry", *J. Am. Chem. Soc.* 1999, 121, pp. 3246-3247.

Li, et al., "Water-Soluble Poly(acrylic acid) Grafted Luminscent Silicon Nanoparticles and Their Use as Fluorescent Biological Staining Labels", *Nano Letters*, 2004, vol. 4, No. 8, pp. 1463-1467.

Xu, at al., "Electrophoretic Analysis and Purification of Fluorescent Single-Walled Carbon Nanotube Fragments", *J. American Chemical Society*, 2004, vol. 126, pp. 12736-12737.

Tisler, et al., "Fluorescence and Spin Properties of Defects in Single Digit Nanodiamonds", *ACSNANO*, 2009, vol. 3, No. 7, pp. 1959-1965.

Ray, et al., "Fluorescent Carbon Nanoparticles: Synthesis, Characterization, and Bioimaging Application", *J. Phys. Chem. C.*, 2009, vol. 113, pp. 18546-18551.

Tian, et al., "Nanosized Carbon Particles From Natural Gas Soot", *Chemistry of Materials*, 2009, vol. 21, pp. 2803-2809.

Mao, et al. "Study on the fluorescence characteristics of carbon dots", *Spectrochimica Acta Part A*, Part A, 2010, Vo. 75, pp. 553-557.

* cited by examiner

4A

4B

4C

FLUORESCENT CARBON NANOPARTICLES

CROSS REFERENCE TO RELATED APPLICATION

The present application claims filing benefit of U.S. provisional patent application Ser. No. 60/730,790 filed on Oct. 27, 2005, which is hereby incorporated by reference in its entirety.

BACKGROUND

Particles having extremely large surface area to volume ratios can exhibit unique and often surprising characteristics. In particular, nanoparticles, i.e., particles of less than about 100 nm in size, can exhibit properties including physical, electronic, optical, and catalytic properties unequaled by their macroscopic counterparts. The formation of light emitting nanoparticles is one area where this phenomenon is being taken advantage of. For instance, light emitting nano-sized particles have been proposed for use in measuring and sensing applications, in light emitting display devices, and in coherent light generation and optical gain applications, among others.

Known light emitting nanoparticles are either silicon nanoparticles or luminescent quantum dots. Silicon nanoparticles are not naturally luminescent, but can be surface treated to exhibit photoluminescence, usually via oxidation and optionally followed by addition of a secondary material to form a desired surface end group. Quantum dots are fluorescent semi-conductor or metal nanoparticles that can be passivated and/or capped to obtain the desired optical and physical characteristics. In either case, the materials and/or formation methods are usually expensive, complicated, and often suitable for forming only very small amounts of the luminescent materials. Moreover, many of the materials, for instance lead- or cadmium-containing semiconductor materials, are less than attractive for medical or biological-based applications due to possible toxicity of the materials.

What is need in the art are luminescent materials that can be formed from inexpensive, abundant starting materials and according to relatively simple, inexpensive methods. Moreover, what is need in the art are formation methods that can be scaled up to provide large quantities of the luminescent materials.

SUMMARY

In one embodiment, the disclosed subject matter is directed to a photoluminescent nanoparticle that includes a carbon core of a size less than about 100 nm. For example, the carbon care can include amorphous carbon. The carbon core can be smaller, in some embodiments. For example, the carbon core can be less than about 30 nm in size, or between about 1 nm and about 10 nm in size.

Coupled to the carbon core can be a passivation agent. A passivation agent can be, for example, a polymer or a biopolymer. The passivation agent can be coupled to the carbon core in any suitable fashion such as, for example, covalent bonding between the two. In one embodiment, a passivation agent can retain a reactive functionality.

A photoluminescent nanoparticle as described herein can include additional materials. For example, a material (e.g., a metal or a magnetic material) can be embedded in or on the carbon core. In one embodiment, a member of a specific binding pair can be bound to the passivation agent, for instance via a reactive functional chemistry retained on the passivation agent following binding of the passivation agent to the carbon core.

In another embodiment, the disclosed subject matter is directed to methods of forming a photoluminescent carbon nanoparticle. Methods can include, for instance, forming a carbon core, for example via laser ablation of graphite or electric arc discharge of a carbon powder. A formation method can include coupling a passivation agent to a carbon core according to any suitable method. In one embodiment, a formation method can include binding an additional material, for instance a member of a specific binding pair, to a carbon nanoparticle, for instance via the passivation agent.

A photoluminescent carbon nanoparticle can be used in many applications. For example, a photoluminescent carbon nanoparticle can be used to detect a compound in a test sample by contacting a sample with a carbon nanoparticle and binding a compound that is in the sample to the carbon nanoparticle to form a complex. The compound can then be detected by the photoluminescent properties of the complex.

In particular, the photoluminescent properties of the complex can differ from those of the compound, the carbon nanoparticle, or both. For example, the starting carbon nanoparticle can be photoluminescent and upon binding with the compound, those photoluminescent properties can be quenched such that the formed complex exhibits little or no luminescence. In another embodiment, the starting carbon nanoparticle can exhibit little or no photoluminescence and the compound can act as a passivation agent such that upon formation of the complex, the complex exhibits photoluminescence. In yet another embodiment, a photoluminescent carbon nanoparticle can tag a non-luminescent compound and the complex can also be photoluminescent and thus detectable.

Exemplary compounds that can bind to a carbon nanoparticle as described herein can include, without limitation, a compound at a surface of a living organism (e.g., a cell surface receptor), a biologically active material, or an environmentally hazardous substance.

BRIEF DESCRIPTION OF THE FIGURES

A full and enabling disclosure of the present subject matter, including the best mode thereof, to one of ordinary skill in the art, is set forth more particularly in the remainder of the specification, including reference to the accompanying figures, in which.

DETAILED DESCRIPTION

Figure 1:
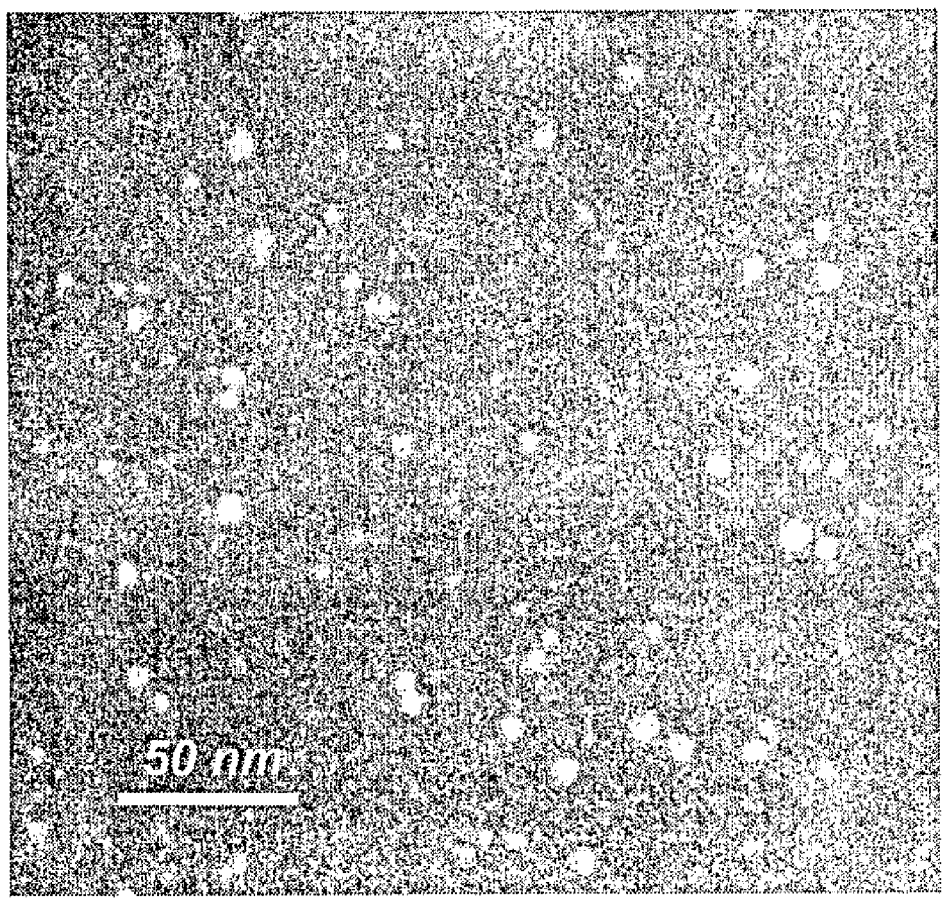
FIG. 1 is a transmission electron microscopy (TEM) image (dark field) of carbon nanoparticles coated with $PEG_{1500N}$ as described in Example 1.

Reference will now be made in detail to various embodiments of the disclosed subject matter, one or more examples of which are set forth below. Each embodiment is provided by way of explanation, not limitation, of the subject matter. In fact, it will be apparent to those skilled in the art that various modifications and variations may be made without departing from the scope or spirit of the disclosure. For instance, features illustrated or described as part of one embodiment, may be used in another embodiment to yield a still further embodiment.

The present disclosure is generally directed to luminescent nanoparticles and methods for forming the luminescent nanoparticles. In particular, luminescent nanoparticles herein disclosed can be photoluminescent and can include a core of a carbon nanoparticle and one or more materials bound to the surface of the carbon nanoparticle.

While not wishing to be bound by any particular theory, it is believed that the electronic states of disclosed nanoparticles can be understood from a combination of both quantum confinement effects and surface passivation effects. Specifically, it is believed that a combination of both quantum confinement and surface passivation can determine the properties of the electronic states of the nanoparticles, and under suitable excitation, nanoparticles as herein disclosed can become strongly luminescent. Accordingly, it is believed that particular characteristics of disclosed materials can not only depend upon the size of a particle, but also upon the material(s) bound to the surface of the carbon nanoparticle. For example, some variation in luminescent characteristics of a particle can be attained through variation of the particular material(s) bound to the surface of the carbon nanoparticle.

For purposes of the present invention, the term 'surface passivation' refers to the stabilization of the surface of a nanoparticle and is herein defined to include any process in which reactive bonds on the surface of a nanoparticle are terminated and rendered chemically passive. Hence, the term can include elemental passivation, in which a passivating element is bound to an existing bond on a surface, as well as the more generic concept of passivation in which a material can be bound to a surface through formation of a covalent bond between the surface and the material, with the possibility of the survival of bonding sites still existing at the surface following the passivation reaction. In this second instance, for example, the passivating material can be a polymer, and the passivation process can form a shell or coating over at least a portion of the surface of a nanoparticle. This shell or coating can be covalently bound to the nanoparticle surface at multiple locations, though not necessarily so as to render every reactive bond on the surface chemically passive.

A core carbon nanoparticle can be formed according to any suitable process capable of forming a carbon particle on a nanometer scale. For example, in one embodiment, a core carbon nanoparticle can be formed from an amorphous carbon source, such as carbon black; from graphite, for instance in the form of graphite powder; or from crystalline carbon (e.g., diamond). For example, according to one embodiment, a core carbon nanoparticle can be formed according to a laser ablation method from a graphite starting material. In another embodiment, a core carbon nanoparticle can be formed in an electric arc discharge from carbon powders. Other methods can be utilized as well, for instance, thermal carbonization of particles of carbon-rich polymers. Such methods are generally known to those of ordinary skill in the art and thus are not described in detail herein.

A carbon nanoparticle can generally be any size from about 1 nm to about 100 nm in average diameter. While not wishing to be bound by any particular theory, it appears that there is quantum confinement effect on the observed luminescence of the materials, and in particular, a relatively large surface area to volume ratio is required in order to confine the recombination of excitons to the surface of a nanoparticle. Accordingly, it appears that higher luminescence quantum yields can be achieved with a smaller core carbon nanoparticle as compared to a larger nanoparticle having the same or similar surface passivation. As such, a luminescent particle including a relatively larger core carbon nanoparticle, e.g., greater than about 30 nm in average diameter, can be less luminescent than a smaller particle. In one embodiment, a core carbon nanoparticle can be less than about 20 nm in average diameter, for instance, in one particular embodiment, between about 1 and about 10 nm in average diameter.

In order to attain the ability to exhibit photoluminescence, a passivation agent can be bound to the surface of a carbon nanoparticle. A passivation agent can be any material that can bind to a carbon nanoparticle surface and encourage or stabilize the radiative recombination of excitons, which is believed to come about through stabilization of the excitation energy 'traps' existing at the surface as a result of quantum confinement effects and the large surface area to volume ratio of a nanoparticle. The agent(s) can be bound to a nanoparticle surface according to any binding methodology. For example, a passivation agent can bind to a nanoparticle surface covalently or noncovalently or a combination of covalently and noncovalently. Moreover, a passivation agent can be polymeric, molecular, biomolecular, or any other material that can passivate a nanoparticle surface. For instance, the passivation agent can be a synthetic polymer such as poly (lactic acid) (PLA), poly(ethylene glycol (PEG), poly(propionylethylenimine-co-ethylenimine) (PPEI-EI), and poly (vinyl alcohol) (PVA). In one embodiment, the passivation agent can be a biopolymer, for instance a protein or peptide. Other exemplary passivation agents can include molecules bearing amino and other functional groups.

The passivation agent and/or additional materials grafted to the core nanoparticle via the passivation agent (exemplary embodiments of which are discussed in more detail below) can provide the luminescent particles with additional desirable characteristics. For example, a hydrophilic passivation agent can be bound to the core carbon nanoparticle to improve the solubility/dispersibility of the nanoparticles in water. In another embodiment, a passivation agent can be selected so as to improve the solubility of the carbon nanoparticle in an organic solvent.

In one particular embodiment, a core carbon nanoparticle can be mostly amorphous. Due to the presence of localized π electrons and the existence of dangling bonds on an amorphous carbon particle, a passivating material of this embodiment can be any number of possible materials. In fact, it is currently understood that a carbon nanoparticle can be passivated and attain the capability of exhibiting photoluminescence upon the binding of any material capable of covalently, noncovalently or a combination of covalently and noncovalently bonding at a surface of a carbon nanoparticle. In particular, there is no particular limitation to the type of passivation agents or the surface end group formed according to the passivation reaction.

In one embodiment, a core carbon nanoparticle can include other components, in addition to carbon. For example, metals and/or other elements can be embedded in a core carbon nanoparticle. In one particular embodiment, a magnetic metal along or in combination with other materials, such as, for example, Ni/Y, can be embedded in a core carbon nanoparticle. For example, the addition of the desired materials, e.g., a metal powder, to the carbon core can be attained through the addition of the materials during the formation process of the carbon particles and the material can thus be incorporated into the core (see, e.g., Example 3). Upon the functionalization of such a nanoparticle to provide surface passivation, the resulting luminescent carbon nanoparticle that includes an embedded metal, e.g., an embedded magnetic metal, can be magnetically responsive, which can be useful in many applications including, for example magnetic detection, precipitation and separation, signaling, and the like.

In one embodiment, a carbon nanoparticle can be formed to include a reactive functional chemistry suitable for use in a desired application, e.g., a tagging or analyte recognition protocol. For instance, a passivating agent can include a reactive functionality that can be used directly in a protocol, for example to tag a particular analyte or class of materials that may be found in a sample. Exemplary materials can include, for example, carbohydrate molecules that may conjugate with carbohydrates on an analyte or biological species.

In another embodiment, a functional chemistry of a passivation agent can be further derivatized with a particular chemistry suitable for a particular application. For example, in one embodiment, a reactive functionality of a passivating agent can be further derivatized via a secondary surface chemistry functionalization to serve as a binding site for substance. For example, a member of a specific binding pair, i.e., two different molecules where one of the molecules chemically and/or physically binds to the second molecule, such as an antigen or an antibody can be bound to a nanoparticle either directly or indirectly via a functional chemistry of the passivation agent that is retained on the nanoparticle following the passivation of the core carbon nanoparticle. The passivation and further derivatization of the core carbon nanoparticle need not be carried out in separate reactions steps, however, and in one embodiment, the passivation and derivatization of the carbon nanoparticle can be carried out in a single process step.

Accordingly, a luminescent carbon nanoparticle can be advantageously utilized to tag, stain or mark materials, including biologically active materials, e.g., drugs, poisons, viruses, antibodies, antigens, proteins, and the like; biological materials themselves, e.g., cells, bacteria, fungi, parasites, etc; as well as environmental materials such as gaseous, liquid, or solid (e.g., particulates) pollutants that may be found in a sample to be analyzed. For example, the passivating material can include or can be derivatized to include functionality specific for surface receptors of bacteria, such as $E.\ coli$ and $L.\ monocytogenes$, for instance. Upon recognition and binding, the bacteria can be clearly discernable due to the photoluminescent tag bound to the surface.

Suitable reactive functionality particular for targeted materials are generally known to those of skill in the art. For example, when considering development of a protocol designed for recognition or tagging of a particular antibody in a fluid sample, suitable ligands for that antibody such as haptens particular to that antibody, complete antigens, epitopes of antigens, and the like can be bound to the polymeric material via the reactive functionality of the passivating material.

In another embodiment, a nanoparticle can be utilized to tag or mark the presence of a particular substance through the development of the photoluminescent characteristic on the nanomaterials only when the nanoparticle is in the presence of the targeted substance. For example, a carbon nanoparticle can be formed and not subjected to a passivation reaction or optionally only partially passivated, such that the nanoparticle exhibits little or no photoluminescence. Upon contact with a passivating material (e.g., a targeted substance) under reaction conditions, the nanoparticle can be passivated by the targeted substance in the sample and the nanoparticle can then exhibit increased photoluminescence, and the presence of the targeted substance can be confirmed via the increased luminescence of the nanoparticle.

In another embodiment, the luminescence from a passivated, highly luminescent carbon nanoparticle can be quenched in the presence of a particular targeted substance. For example, the visible luminescence can be quenched in the presence of a potentially harmful environmental substance such as a nitro-derivatized benzene, TNT, or a key ingredient in explosives. For example, upon contact of the passivated, luminescent nanoparticle with the targeted substance, the luminescent properties of the nanoparticle can be quenched via collision or contact of the quencher molecules (i.e., the detectable substance) with the luminescent carbon nanoparticles that result in electron transfers or other quenching mechanisms as are generally known to those in the art.

A photoluminescent nanoparticle can obviously be utilized in many other applications as well, in addition to tagging and recognition protocols such as those described above. For example, the disclosed luminescent nanoparticles can generally be utilized in applications previously described as suitable for photoluminescent silicon nanoparticles. In some embodiments, luminescent nanoparticles as herein described can be utilized in applications suitable for luminescent nanoparticles. For instance, disclosed luminescent nanoparticles can be utilized in applications such as are common for luminescent quantum dots.

Beneficially, luminescent carbon nanoparticles can be more environmentally and biologically compatible than previously known luminescent nanoparticles. For instance, a luminescent carbon nanoparticle can be formed so as to pose little or no environmental or health hazards during use, hazards that exist with many previously known luminescent nanoparticles. As such, a luminescent carbon nanoparticle as described herein can be utilized in light emission applications, data storage applications such as optical storage mediums, photo-detection applications, luminescent inks, and optical gratings, filters, switches, and the like, just to name a few possible applications as are generally known to those of skill in the art, and can be more ecologically friendly than many previously known luminescent nanoparticles.

Moreover, as disclosed carbon-based materials can emit different colors at different excitation wavelengths, they can be used economically in practical, real-world applications. For instance, in using disclosed carbon-based materials in labeling applications, detection and/or analysis (for instance through utilization of confocal fluorescence microscopy) can be performed at multiple colors without the need for multiple sets of different luminescent materials.

The present invention may be better understood by reference to the examples set forth below.

EXAMPLE 1

Carbon particles were produced via laser ablation of a graphite powder carbon target in the presence of water vapor (argon was used as the carrier gas) according to standard methods as described by Y. Suda, et al. (*Thin Solid Films*, 415, 15 (2002), which is incorporated herein by reference). The as-produced sample contained only nanoscale carbon particles according to results from electron microscopy analyses. The particles exhibited no detectable luminescence in suspension or solid-state and neither before nor after an oxidative acid treatment (refluxed in 2.6M aqueous nitric acid solution for 12 hours).

Following the oxidative acid treatment, the particle sample was mixed with diamine-terminated polyethylene glycol, $H_2NCH_2(CH_2CH_2O)_nCH_2CH_2CH_2NH_2$ (average n~35, $PEG_{1500N}$). The mixture was then held at 120° C. with agitation for 72 hours. Following this, the sample was cooled to room temperature and then water was added, followed by centrifuging. The homogeneous supernatant contained the surface passivated carbon nanoparticles. TEM and AFM characterization showed the nanoparticles to have diameters between about 5 nm and about 10 nm. FIG. 1 is a TEM dark field image of the passivated nanoparticles.

Figure 2:
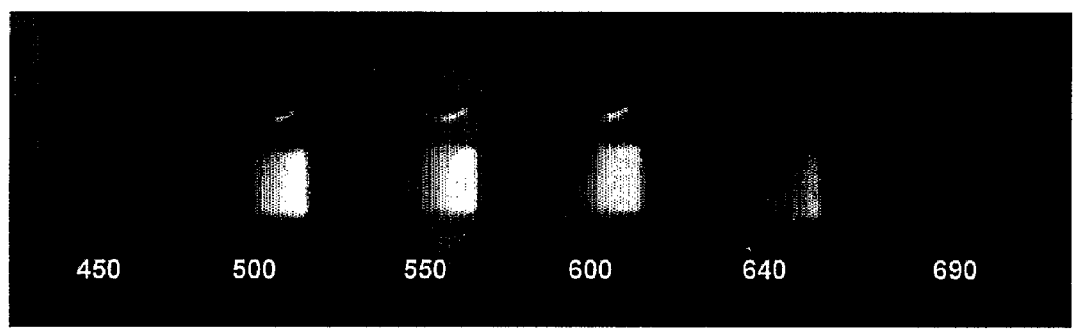
FIG. 2 includes a series of photographs of an aqueous solution of the $PEG_{1500N}$ coated carbon nanoparticles of Example 1 excited at 400 nm and photographed through different band-pass filters.
Figure 3:
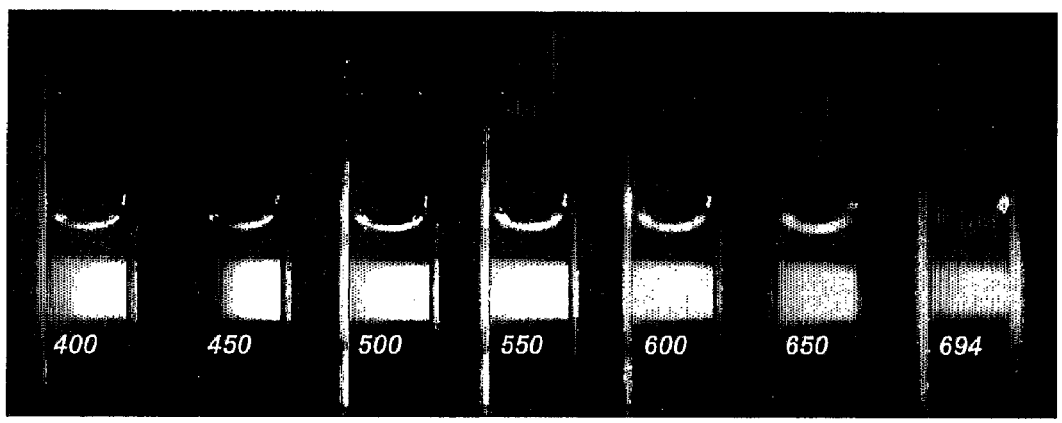
FIG. 3 is a series of photographs of an aqueous suspension of the $PEG_{1500N}$ coated carbon nanoparticles of Example 1 excited at various wavelengths and photographed directly.
Figure 4:
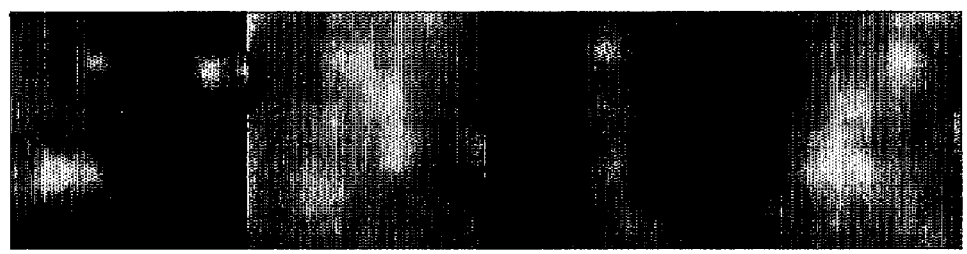
FIG. 4A-4C are confocal microscopy images of the $PEG_{1500N}$ coated carbon nanoparticles of Example 1 excited at different excitation wavelengths and with different band-pass filters.
Figure 4:
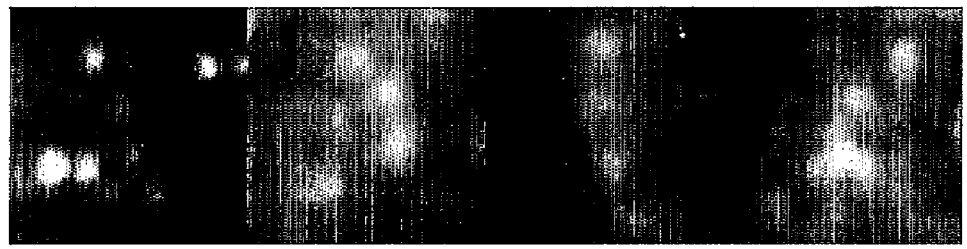
Figure 4:

The surface-passivated carbon nanoparticles were found to be strongly luminescent both in a solution-like suspension and in the solid state. For example, and with reference to the attached figures, FIGS. 2 and 3 illustrate a sample of the $PEG_{1500N}$ coated carbon nanoparticles in an aqueous suspension. In FIG. 2, the samples were excited at 400 nm and photographed through different band-pass filters of 450, 500, 550, 600, 640 and 690 nm, as indicated. FIG. 3 is a series of photographs of the $PEG_{1500N}$ coated carbon nanoparticles in the aqueous suspension excited at increasing wavelengths of 400, 450, 500, 550, 600, 650, and 694 nm, as indicated on the figure, and photographed directly. FIGS. 4A-4C are confocal microscopy images of the $PEG_{1500N}$ coated carbon nanoparticles excited at different excitation wavelengths and with different band-pass filters, as indicated on the Figure. Specifically, in FIG. 4A (top) $\lambda_{ex}$=458 nm with 505 nm longpass filter; FIG. 4B (middle) $\lambda_{ex}$=488 nm with 530 nm longpass filter; and FIG. 4C (bottom) $\lambda_{ex}$=543 nm with 585 nm longpass filter.

EXAMPLE 2

Figure 5:
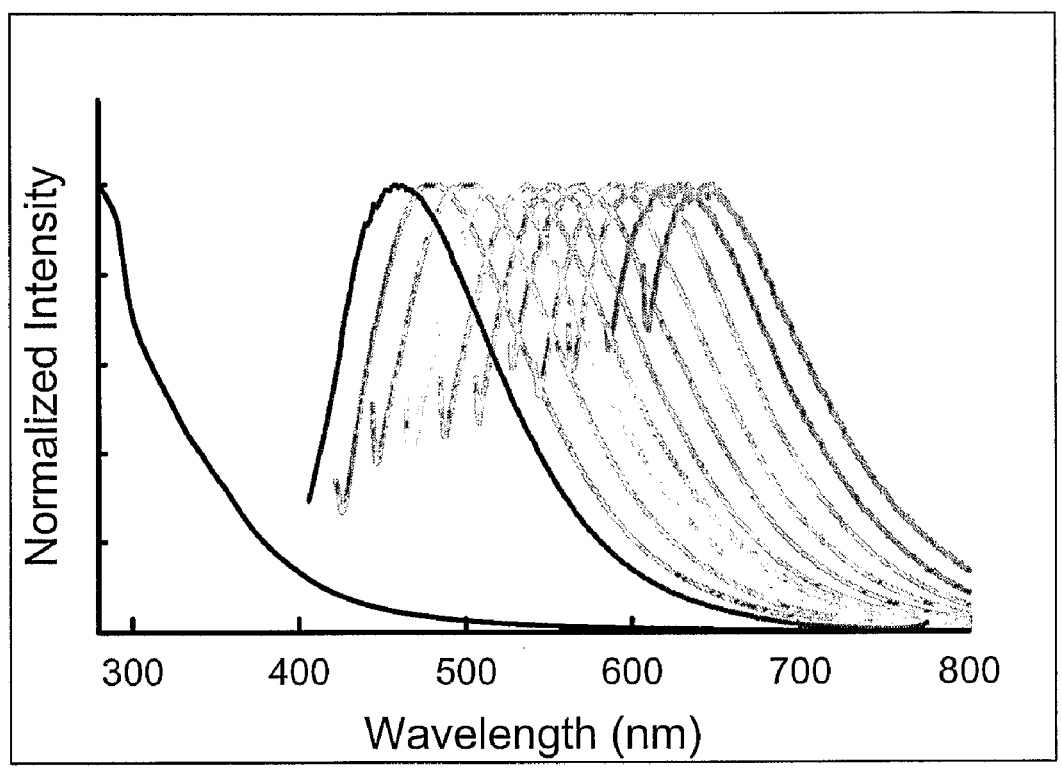
FIG. 5 is the absorption and emission spectra of carbon nanoparticles coated with a poly(propionylethylenimine-co-ethylenimine) (PPEI-EI) copolymer, as described in Example 2.

The same protocol as described above was performed, but for the utilization of poly(propionylethylenimine-co-ethylenimine) (PPEI-EI) as the passivation agent. FIG. 5 illustrates the absorption and emission spectra of the PPEI-EI passivated particles. In particular, the particles were excited with a 400 nm excitation wavelength (on the left), and with progressively longer excitation wavelengths increasing in 20 nm increments.

The observed luminescence quantum yields for both examples were found to be of from about 5% to more than about 10%, depending upon the excitation wavelength, the particular passivation agent used, and the medium. These yields are comparable to those of previously known silicon nanocrystals. The luminescence was also found to be stable with respect to photoirradiation, exhibiting no meaningful reduction in the observed intensities in continuously repeating excitations over several hours.

As can be seen with reference to the Figures, the luminescence of the materials can cover a broad wavelength region in the visible and can extend into the near-infrared, suggesting a distribution of emissive species and/or sites. Such a distribution can also allow the selection of different luminescence colors with the use of different excitation wavelength with a single sample of materials, as illustrated in the figures.

EXAMPLE 3

Figure 6:
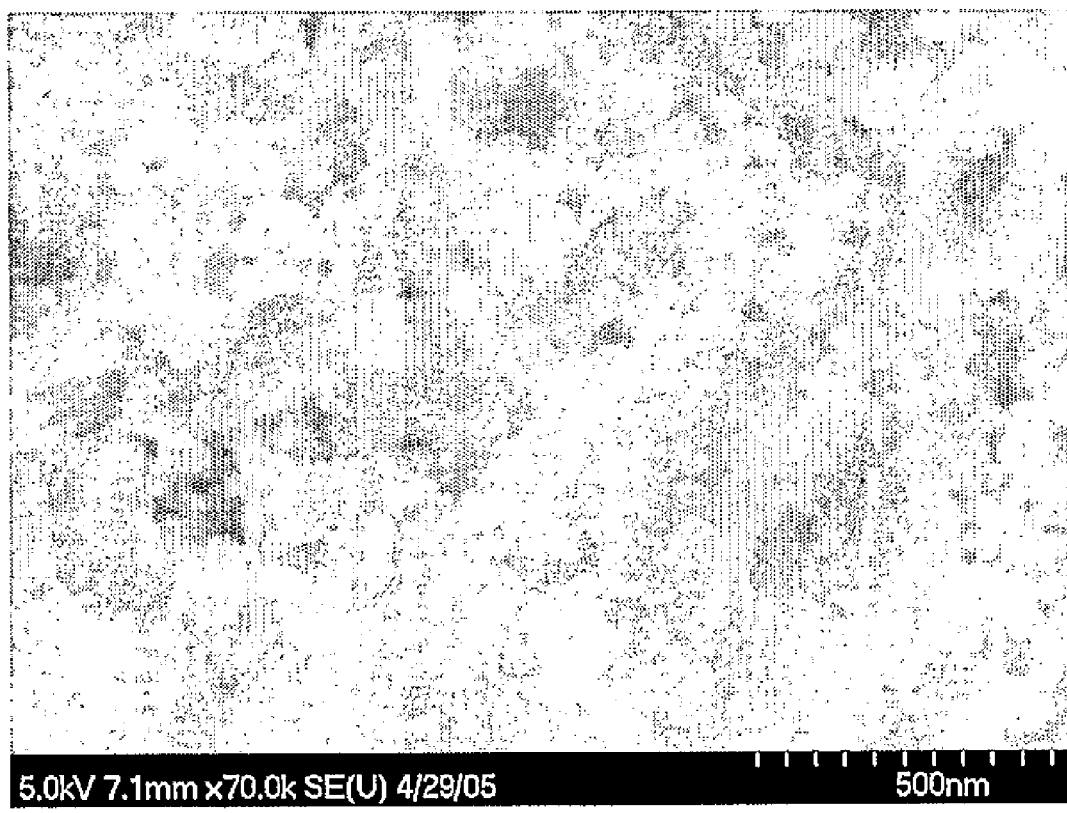
FIG. 6 is an SEM image of as-produced (from arc-discharge method) carbon nanoparticles embedded with Ni/Y.

Carbon nanoparticles embedded with Ni/Y were prepared in an electric arc-discharge apparatus. The arc was generated between two electrodes in a reactor under a helium atmosphere (760 Torr). The anode was a hollow graphite rod (6 mm outer diameter, 3 mm inner diameter, and 200 mm long) filled with a mixture of Ni, $Y_2O_3$, and graphite powders, so that the overall compositions of the rod were ~4% Ni, ~1% Y, and ~95% carbon. The arc discharge was created by a current of 90 Amp. A voltage drop of 35V between the electrodes was maintained by an automated welding controller to keep a constant distance (about 0.5 mm) between the cathode and the anode being consumed. The product nanoparticles are illustrated in the SEM in FIG. 6.

EXAMPLE 4

Figure 7A:
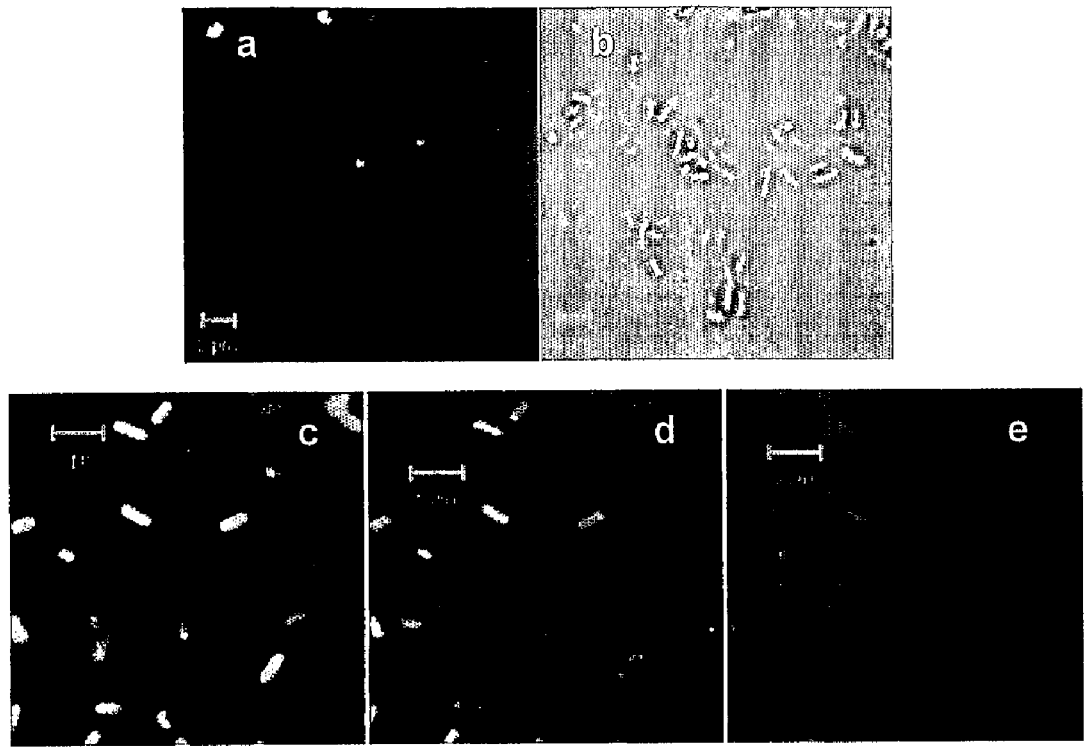
FIG. 7A are microscopy images for the luminescence labeling of *L. monocytogene* Scott A cells with PEG$_{1500N}$-functionalized carbon nanoparticles (FIG. 7A*a*: confocal, and FIG. 7A*b*: bright field); and for the same labeling of *E. coli* ATCC 25922 cells in the confocal imaging with different excitation/long-path detection filter of (FIG. 7A*c*) 458/475 nm, (FIG. 7A*d*) 477/505 nm, and (FIG. 7A*e*) 514/560 nm.

In the labeling of bacterial cells with luminescent carbon nanoparticles, $PEG_{1500N}$-functionalized carbon nanoparticles were used to interact with *E. coli* ATCC 29522 cells. In a typical experiment, an *E. coli* cell solution in PBS (200 μL, ~$10^8$ cfu/mL) was mixed with the solution of $PEG_{1500N}$-functionalized carbon nanoparticles (75 μL), and the mixture was gently rotated for 24 h. Then, the mixture was centrifuged at 10,000 rpm for 10 min, and the sediment was collected and re-suspended for microscopy characterization (FIG. 7A).

The same experimental procedure was used for the binding of $PEG_{1500N}$-functionalized carbon nanoparticles with *L. monocytogene* Scott A cells and *E. coli* ATCC 25922 cells. FIG. 7A*a* illustrates confocal, and FIG. 7A*b* bright field images following luminescence labeling of the *L. monocytogene* Scott A cells with the $PEG_{1500N}$-functionalized carbon nanoparticles. FIGS. 7A*c*, 7A*d*, and 7A*e*, show the products following the same labeling process for *E. coli* ATCC 25922 cells in the confocal imaging with different excitation/long-path detection filter of (7A*c*) 458/475 nm, (7A*d*) 477/505 nm, and (7A*e*) 514/560 nm.

Figure 7B:
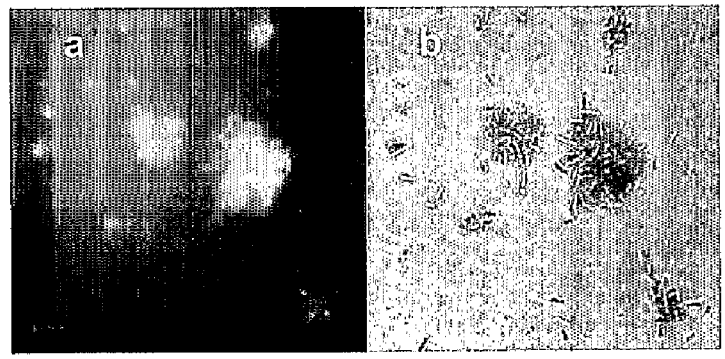
FIG. 7B are confocal (FIG. 7B*a*) and bright-field (FIG. 7B*b*) images for the luminescence labeling of pathogenic *E. coli* O157:H7 cells through the specific targeting with the immuno-carbon nanoparticles (anti-*E. coli* O157 coating)

The luminescent carbon nanoparticles were coated with pathogen-specific antibodies to obtain immuno-carbon nanoparticles. In a typical experiment, $PEG_{1500N}$-functionalized carbon nanoparticles (2 mg), succinic anhydride (18 mg, 1.84 mmol), and DMAP (1 mg, 0.008 mmol) were dissolved in dry $CH_2Cl_2$ (5 mL). After stirring at room temperature for 24 h, the solvent was removed and the crude product was re-dissolved in deionized water (2 mL). The aqueous solution was transferred to a cellulose membrane tubing (MWCO~1,000) for dialysis against fresh deionized water for 2 days to obtain $PEG_{1500N}$-functionalized carbon nanoparticles with carboxylic acids as terminal groups. After the removal of water, the acid-terminated particles were re-suspended in MES buffer (1 mL, pH 6.1). To the suspension was added EDAC (54 mg) and NHS (70 mg), and the mixture was kept at room temperature for 24 h. The solution was dialyzed (MWCO~1,000) against fresh deionized water for 24 h. After solvent removal, the product was re-dissolved in PBS buffer (0.5 mL, pH~7.4), mixed with a solution of affinity purified goat anti-*E. coli* O157 IgG, and gently shaken for 24 h to obtain the immuno-carbon nanoparticles. These particles target pathogenic *E. coli* O157:H7 cells specifically. By applying the same experimental protocol described above, the binding of the immuno-carbon nanoparticles with *E. coli* O157:H7 cells were observed in the microscopy images shown in FIG. 7B including confocal (FIG. 7B*a*) and bright-field (FIG. 7B*b*) images for the luminescence labeling of pathogenic *E. coli* O157:H7 cells.

EXAMPLE 5

Figure 8:
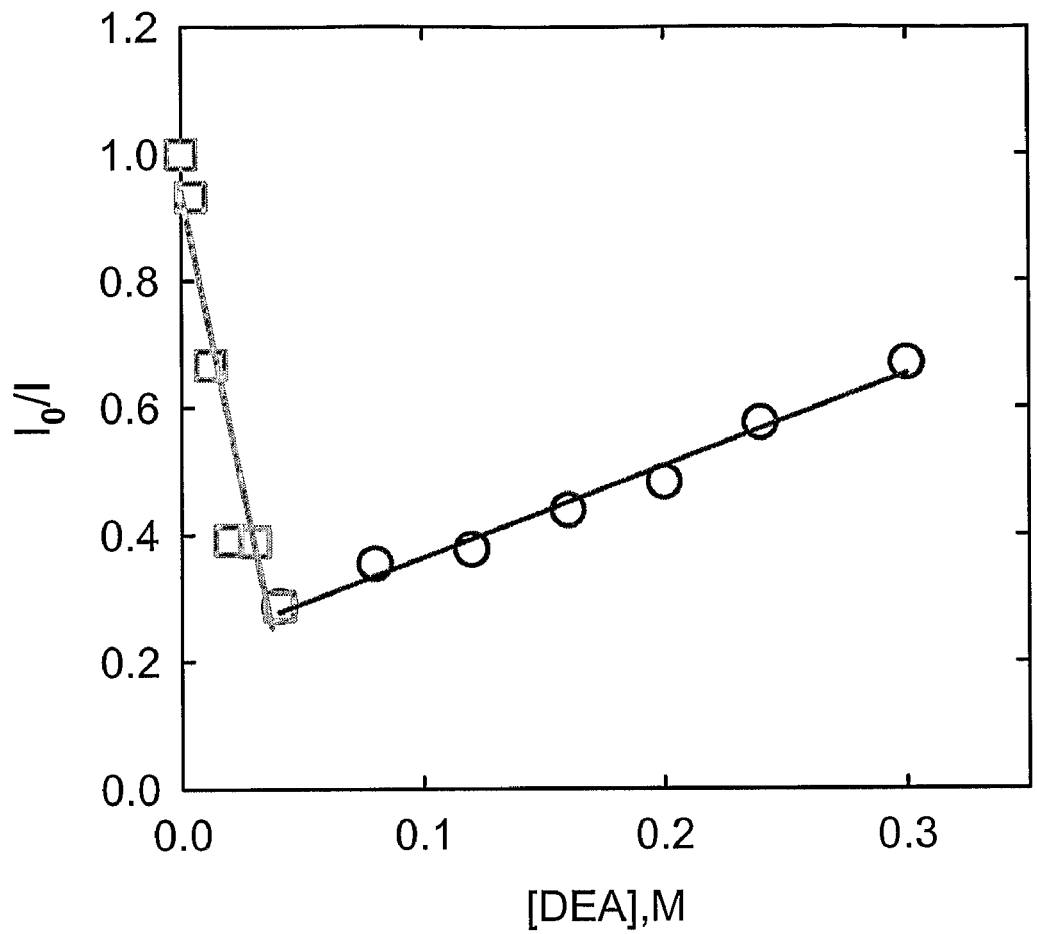
FIG. 8 illustrates a plot of the luminescence quenching ratio (intensity without quencher)/(intensity with quencher), $I_0/I$, for PEG$_{1500N}$-functionalized carbon nanoparticles as a function of the quencher N,N-diethylaniline (DEA) concentration.

Photoluminescence spectra of $PEG_{1500N}$-functionalized carbon nanoparticles were measured in room-temperature chloroform solution in the presence of N,N-diethylaniline (DEA) at different concentrations. While the observed luminescence spectral profiles were unchanged, the intensities were found to increase with the increasing DEA concentration (reversed Stern-Volmer quenching behavior) to reach a maximum at the DEA concentration of approximately 40 mM, and then decreased with additional increase in DEA concentration (normal Stern-Volmer quenching behavior). This is clearly illustrated by the quenching plot in FIG. 8 of the luminescence quenching ratio (intensity without quencher)/(intensity with quencher), $I_0/I$, for $PEG_{1500N}$-functionalized carbon nanoparticles as a function of the quencher N,N-diethylaniline (DEA) concentration.

EXAMPLE 6

Figure 9:
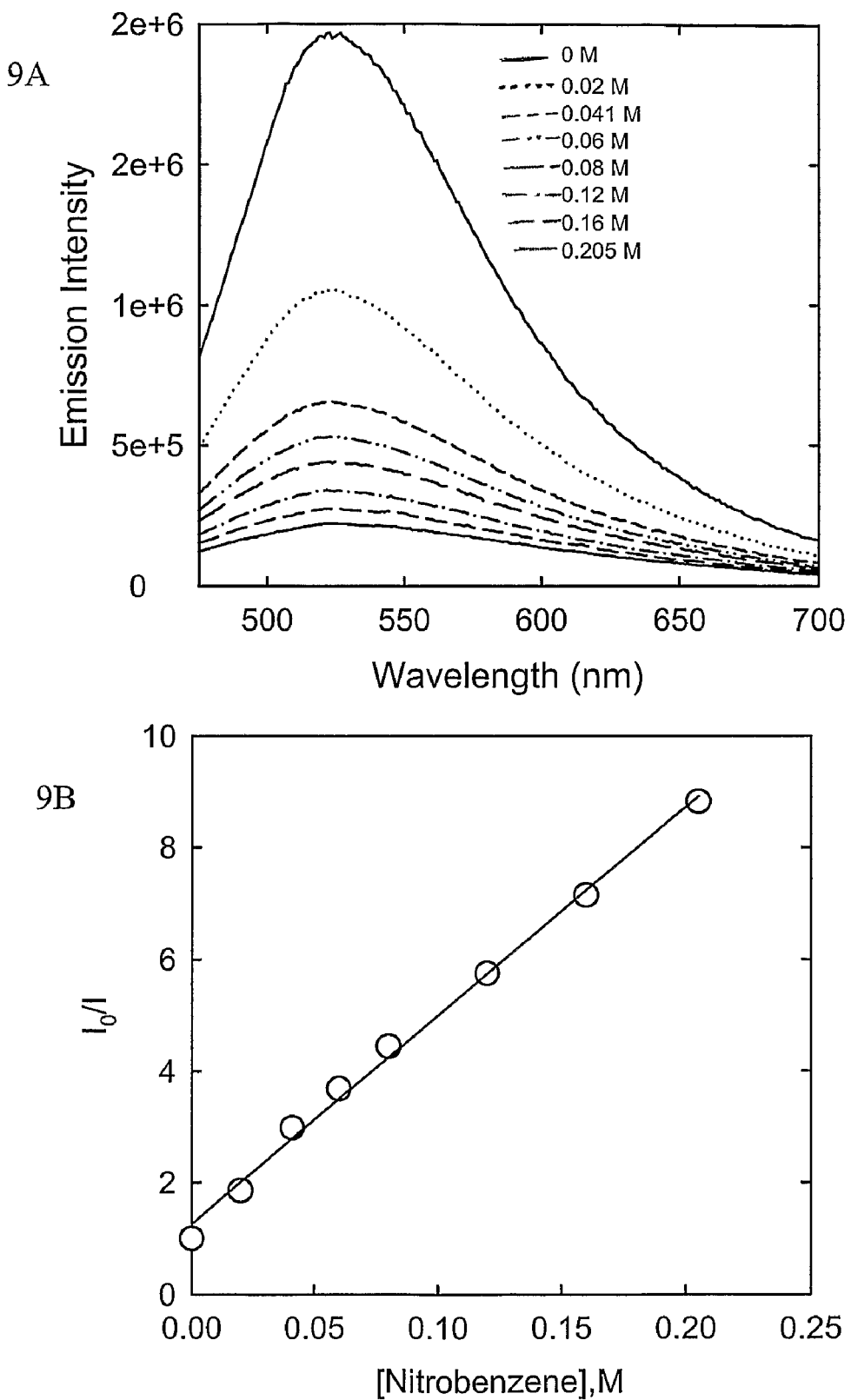
FIG. 9 illustrates the luminescence quenching of PEG$_{1500N}$-functionalized carbon nanoparticles in ethanol solution by nitrobenzene (A: spectral intensities decrease with the increasing quencher concentration; and B: the Stern-Volmer plot).

The same luminescence quenching protocol as described above was performed, but for the utilization of nitrobenzene as the quencher in ethanol solution. The luminescence spectra are little affected by the quencher at different concentrations (FIG. 9A showing the spectral intensities decrease with the increasing quencher concentration; and FIG. 9B showing the Stern-Volmer plot). The quenching follows the normal Stern-Volmer behavior, namely that the luminescence intensities decrease with the increasing quencher concentration. The quenching is also highly efficient, with quenching rate constant approaching the limit of diffusion control (approximately $10^{10}$ $M^{-1}s^{-1}$, FIG. 9).

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A nanoparticle comprising a carbon core and a passivation agent coupled to the carbon core, wherein the carbon core is less than about 100 nanometers in size, the carbon core defining a surface, the carbon core comprising excitation energy traps existing at the surface, wherein the carbon core surface is photoluminescent due to the presence of the passivation agent coupled to the carbon core, the passivation agent stabilizing the excitation energy traps.

2. The nanoparticle of claim 1, wherein the carbon core comprises amorphous carbon.

3. The nanoparticle of claim 1, wherein the carbon core is less than about 30 nanometers in size.

4. The nanoparticle of claim 1, wherein the carbon core is between about 1 and about 10 nanometers in size.

5. The nanoparticle of claim 1, wherein the passivation agent is a polymer.

6. The nanoparticle of claim 1, wherein the passivation agent is a biopolymer.

7. The nanoparticle of claim 1, wherein the passivation agent is covalently bonded to the carbon core.

8. The nanoparticle of claim 1, the nanoparticle further comprising a material embedded in the carbon core.

9. The nanoparticle of claim 8, wherein the material is a metal.

10. The nanoparticle of claim 8, wherein the material is magnetic.

11. The nanoparticle of claim 1, wherein the passivation agent comprises reactive functionality.

12. The nanoparticle of claim 1, wherein the nanoparticle further comprises a member of a specific binding pair bound to the passivation agent.

13. The nanoparticle of claim 1, wherein the passivation agent comprises a protein or a peptide.

14. The nanoparticle of claim 1, wherein the passivation agent is bound to a drug.

15. The nanoparticle of claim 1, wherein the passivation agent is an element.

16. The nanoparticle of claim 1, wherein the passivation agent is a molecular passivation agent.

17. The nanoparticle of claim 1, wherein the passivation agent is grafted to the carbon core.

18. The nanoparticle of claim 1, wherein the passivation agent is noncovalently bound to the carbon core.

19. A nanoparticle comprising a carbon core and a passivation agent coupled to the carbon core, wherein the carbon core is less than about 100 nanometers in size and comprises crystalline carbon, the carbon core defining a surface, the carbon core comprising excitation energy traps existing at the surface, wherein the carbon core surface is photoluminescent due to the presence of the passivation agent coupled to the carbon core, the passivation agent stabilizing the excitation energy traps.

20. The nanoparticle of claim 19, wherein the carbon core is less than about 30 nanometers in size.

21. The nanoparticle of claim 19, wherein the carbon core is between about 1 and about 10 nanometers in size.

22. The nanoparticle of claim 19, wherein the passivation agent is a polymer.

23. The nanoparticle of claim 19, wherein the passivation agent is a biopolymer.

24. The nanoparticle of claim 19, wherein the passivation agent is covalently bonded to the carbon core.

25. The nanoparticle of claim 19, the nanoparticle further comprising a material embedded in the carbon core.

26. The nanoparticle of claim 19, wherein the passivation agent comprises reactive functionality.

27. The nanoparticle of claim 19, wherein the nanoparticle further comprises a member of a specific binding pair bound to the passivation agent.

28. The nanoparticle of claim 19, wherein the passivation agent comprises a protein or a peptide.

29. The nanoparticle of claim 19, wherein the passivation agent is bound to a drug.

30. The nanoparticle of claim 19, wherein the carbon core comprises diamond.

31. A nanoparticle comprising a carbon core and a passivation agent coupled to the carbon core, wherein the carbon core is less than about 100 nanometers in size and comprises graphite, the carbon core defining a surface, the carbon core comprising excitation energy traps existing at the surface, wherein the carbon core surface is photoluminescent due to the presence of the passivation agent coupled to the carbon core, the passivation agent stabilizing the excitation energy traps.

32. The nanoparticle of claim 31, wherein the carbon core is less than about 30 nanometers in size.

33. The nanoparticle of claim 31, wherein the carbon core is between about 1 and about 10 nanometers in size.

34. The nanoparticle of claim 31, wherein the passivation agent is a polymer.

35. The nanoparticle of claim 31, wherein the passivation agent is a biopolymer.

36. The nanoparticle of claim 31, wherein the passivation agent is covalently bonded to the carbon core.

37. The nanoparticle of claim 31, the nanoparticle further comprising a material embedded in the carbon core.

38. The nanoparticle of claim 31, wherein the passivation agent comprises reactive functionality.

39. The nanoparticle of claim 31, wherein the nanoparticle further comprises a member of a specific binding pair bound to the passivation agent.

40. The nanoparticle of claim 31, wherein the passivation agent comprises a protein or a peptide.

41. The nanoparticle of claim 31, wherein the passivation agent is bound to a drug.

\* \* \* \* \*